(12) United States Patent
Smith et al.

(10) Patent No.: US 9,204,850 B2
(45) Date of Patent: Dec. 8, 2015

(54) GANTRY WITH SECONDARY SAFETY MECHANISM

(71) Applicant: General Electric Company, Schenectady, WI (US)

(72) Inventors: Brandon Smith, Waukesha, WI (US); Chad Smith, Frankllin, WI (US)

(73) Assignee: General Electric Company, Schenectady, NY (US)

( * ) Notice: Subject to any disclaimer, the term of this patent is extended or adjusted under 35 U.S.C. 154(b) by 123 days.

(21) Appl. No.: 14/171,892

(22) Filed: Feb. 4, 2014

(65) Prior Publication Data

US 2015/0216492 A1   Aug. 6, 2015

(51) Int. Cl.
  *A61B 6/03*   (2006.01)
  *A61B 6/00*   (2006.01)
  *A61B 6/04*   (2006.01)

(52) U.S. Cl.
  CPC . *A61B 6/44* (2013.01); *A61B 6/035* (2013.01); *A61B 6/0407* (2013.01); *A61B 6/4429* (2013.01)

(58) Field of Classification Search
  CPC ...... A61B 6/4435; A61B 6/035; A61B 6/102; A61B 6/44; A61B 6/4429
  See application file for complete search history.

(56) References Cited

U.S. PATENT DOCUMENTS

| | | | |
|---|---|---|---|
| 5,703,921 | A | 12/1997 | Fujita et al. |
| 5,971,334 | A | 10/1999 | Crawshaw et al. |
| 6,590,953 | B2 | 7/2003 | Suzuki et al. |
| 6,805,367 | B1 * | 10/2004 | Heller ........................ 280/87.01 |
| 6,819,737 | B2 | 11/2004 | Suzuki et al. |
| 7,076,018 | B2 | 7/2006 | Russinger |
| 2006/0018437 | A1 * | 1/2006 | Russinger ..................... 378/197 |
| 2007/0019783 | A1 | 1/2007 | Hockersmith et al. |
| 2010/0025591 | A1 * | 2/2010 | Luecke et al. ........... 250/363.05 |

FOREIGN PATENT DOCUMENTS

WO   WO2013/031684   3/2013

OTHER PUBLICATIONS

International Search Report and Written Opinion from corresponding PCT application No. PCT/US2014/056222 dated Dec. 18, 2014; 9 pages.

* cited by examiner

*Primary Examiner* — David J Makiya
*Assistant Examiner* — John Corbett
(74) *Attorney, Agent, or Firm* — Lucas Divine

(57) ABSTRACT

A gantry of a tomography apparatus has a rotary member that is rotatable around an axis. The rotary member carries at least one component attached thereto. The component is attached by primary and secondary attachment mechanisms, with only the primary attachment mechanism engaged during normal operation. The secondary attachment mechanism, a T-slot interface in one embodiment, engages for safety and other reasons when the primary attachment mechanism is not functioning properly.

26 Claims, 8 Drawing Sheets

GANTRY WITH SECONDARY SAFETY MECHANISM

BACKGROUND

The subject matter disclosed herein relates generally to gantry design and, more particularly, safety mechanisms for gantries.

Gantries are an important part of radiography and tomography systems. A medical imaging system can include a gantry comprising a stationary frame for supporting a rotary member about a scanning axis of the scanner. The rotary member includes a central opening large enough to receive a patient extending along the scanning axis. The rotary member is rotated about a patient during a scanning or imaging procedure. An x-ray tube can be positioned on the rotary member diametrically across the central opening from an array of x-ray detectors. As the rotary member rotates, the x-ray tube projects a beam of energy, or x-rays, along a scan plane, through a patient, and to the detector array. By rotating the x-ray source about the scanning axis and relative to the patient, x-rays are projected through a patient from many different directions. An image of the scanned portion of a patient can be constructed from data provided by the detector array using a computer.

X-ray detectors, x-ray tubes, and other components can be attached to the rotary member. These components can be heavy, and the rotary member can be rotated at high speeds. This can create substantial force. Fastening elements attaching the components to the rotary member can be subjected to particularly high stress, especially as the speed of rotation increases. Fastening elements may not be set properly by a technician or installation professional. Fastening elements may bend, break, and/or cause a component to detach from the rotary member. These factors can lead to damage to the radiography or tomography system or endangerment of personnel in its vicinity. A secondary source of attachment is useful for safety and usability.

BRIEF DESCRIPTION

In accordance with an embodiment, a gantry for a tomography system is provided that can comprise a stationary support structure, a rotary member with an opening for insertion of a subject, wherein the rotary member is attached to the support structure, a component, wherein the component can be attached to the rotary member by a primary attachment mechanism, and wherein the component can be attached to the rotary member by a secondary attachment mechanism, the secondary attachment mechanism being a T-slot interface. Further, the system can include a socket securable to a first member and having a base defining a recess bordered by a lip, a fastener having an elongate stem portion securable to a second member and a head slidably insertable into the recess of the socket where it is retained by the lip of the socket, and wherein the first member is the rotary member and the second member is the component, or the first member is the component and the second member is the rotary member. Further, the system can include a latch for securing a t-slot fastener in place to prevent axial movement of the fastener from a t-slot socket, wherein the t-slot fastener includes an angled edge on an insertion side, and the angled edge depresses the latch as the t-slot fastener is slid into the t-slot socket.

In one embodiment, during rotation of the rotary member, the secondary attachment mechanism does not support the weight of the component if the primary attachment mechanism is engaged. If the primary attachment mechanism is not engaged, the secondary attachment mechanism supports the weight of the component. In this case, the t-slot interface can generate a human-audible noise. The secondary attachment mechanism can support partial or full weight of the mechanism if the primary attachment mechanism is weak, faulty, broken, or only partially engaged.

In accordance with an embodiment, a component is provided, including at least one receiving slot to accept a primary attachment mechanism, at least one t-slot fastener as part of a secondary attachment mechanism, and wherein the primary and secondary attachment mechanisms can be used to attach the component to a support structure.

In accordance with an embodiment, a support structure is provided, including at least one receiving slot to accept a primary attachment mechanism, at least one receiving socket as part of a secondary attachment mechanism, the socket having a base defining a recess bordered by a lip, wherein the primary and secondary attachment mechanisms can be used to attach a component to the support structure. The secondary attachment mechanism does not support the weight of the component if the primary attachment mechanism is engaged.

DETAILED DESCRIPTION

Figure 1:
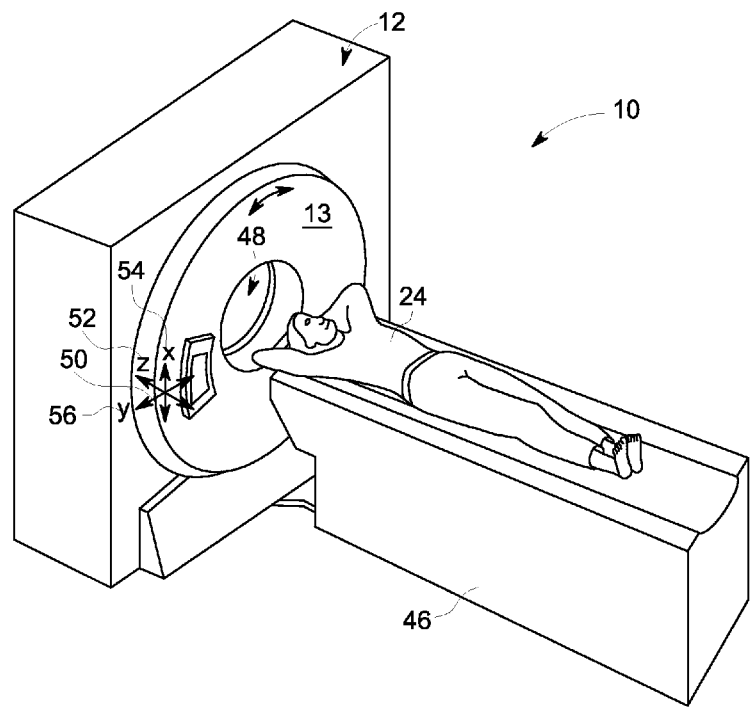
FIG. 1 is an angled view of a medical imaging system with a gantry in accordance with an embodiment.

The foregoing summary, as well as the following detailed description of certain embodiments and claims, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Figure 2:
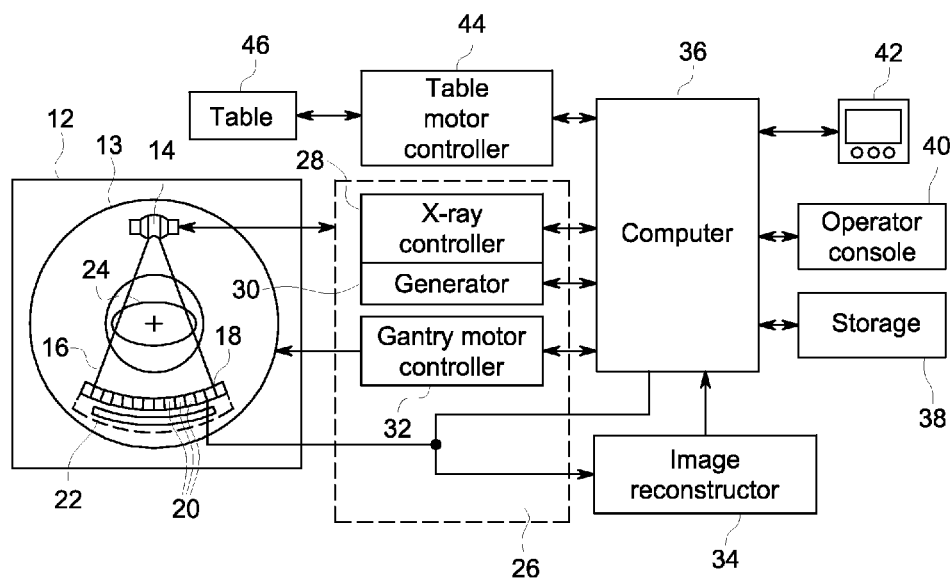
FIG. 2 is a block schematic diagram of a medical imaging system in accordance with an embodiment.

FIGS. 1 and 2 show a computed tomography (CT) imaging system 10 including a gantry 12. Gantry 12 has a rotary member 13 an x-ray source 14 that projects a beam of x-rays 16 toward a detector assembly 18 on the opposite side of the rotary member 13. A main bearing may be utilized to attach the rotary member 13 to the stationary structure of the gantry 12. X-ray source 14 includes either a stationary target or a rotating target. Detector assembly 18 is formed by a plurality of detectors 20 and data acquisition systems (DAS) 22, and can include a collimator. The plurality of detectors 20 sense the projected x-rays that pass through a subject 24, and DAS 22 converts the data to digital signals for subsequent processing. Each detector 20 produces an analog or digital electrical signal that represents the intensity of an impinging x-ray beam and hence the attenuated beam as it passes through subject 24. During a scan to acquire x-ray projection data, rotary member 13 and the components mounted thereon can rotate about a center of rotation.

Rotation of rotary member 13 and the operation of x-ray source 14 are governed by a control mechanism 26 of CT system 10. Control mechanism 26 can include an x-ray controller 28 and generator 30 that provides power and timing signals to x-ray source 14 and a gantry motor controller 32 that controls the rotational speed and position of rotary member 13. An image reconstructor 34 receives sampled and digitized x-ray data from DAS 22 and performs high speed image reconstruction. The reconstructed image is output to a computer 36 which stores the image in a computer storage device 38.

Computer 36 also receives commands and scanning parameters from an operator via operator console 40 that has some form of operator interface, such as a keyboard, mouse, touch sensitive controller, voice activated controller, or any other suitable input apparatus. Display 42 allows the operator to observe the reconstructed image and other data from computer 36. The operator supplied commands and parameters are used by computer 36 to provide control signals and information to DAS 22, x-ray controller 28, and gantry motor controller 32. In addition, computer 36 operates a table motor controller 44 which controls a motorized table 46 to position subject 24 and gantry 12. Particularly, table 46 moves a subject 24 through a gantry opening 48, or bore, in whole or in part. A coordinate system 50 defines a patient or Z-axis 52 along which subject 24 is moved in and out of opening 48, a gantry circumferential or X-axis 54 along which detector assembly 18 passes, and a Y-axis 56 that passes along a direction from a focal spot of x-ray tube 14 to detector assembly 18.

Figure 3:
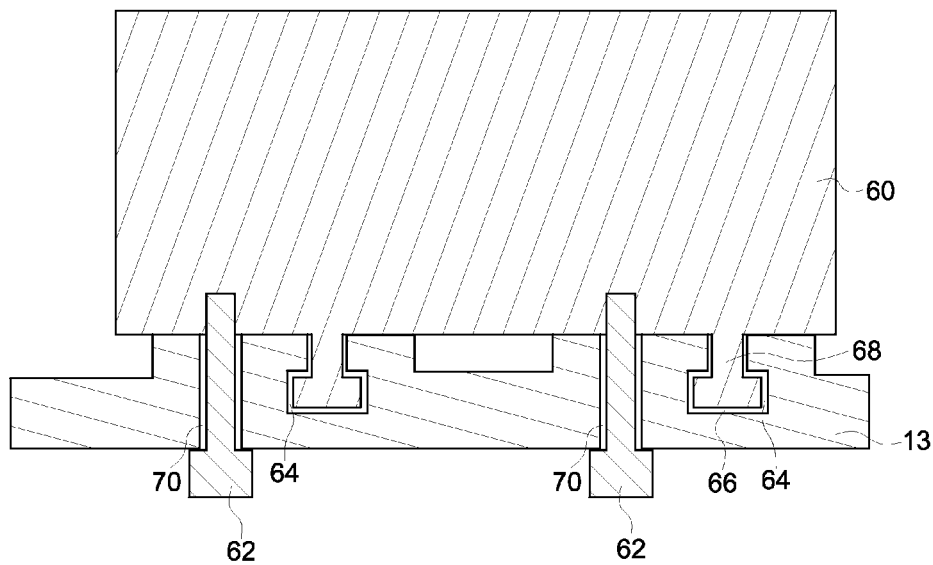
FIG. 3 is a side view of a component attached to a rotary member with primary and secondary attachment mechanisms in accordance with an embodiment.

FIG. 3 shows one view of a rotary member 13 with a component 60 attached thereto, according to one embodiment. Rotary member 13 may also be referred to as a drum or disk. Component 60 can be an x-ray tube, high voltage generator, heat exchanger, collimator, image detector, circuit board chassis, balance weight, power supply, or other item to be attached to rotary member 13.

FIG. 3 shows primary attachment mechanism 62 and secondary attachment mechanism 64 in normal operation conditions. Primary attachment mechanism 62 may be bolts in one embodiment or other types of fastening elements in alternative embodiments. FIG. 3 shows the primary attachment mechanisms 62 attached to component 60 through slots 70. While the primary attachment mechanisms are shown at a perpendicular angle to the rotary member, they can be set at alternative angles or orientations for fastening. In normal operation conditions as shown in FIG. 3, primary attachment mechanism 62 is engaged, thus pressed flush against rotary member 13, to prevent any pulling away of component 60 due to centrifugal, gravitational, or other forces during operation of the medical imaging system. While FIG. 3 shows the sides of primary attachment mechanism 62 as not flush against rotary member 13 in slot 70, the sides can be flush in alternative embodiments. Slot 70 may have threads to accept bolts or screws in one embodiment. While FIG. 3 shows two primary attachment mechanisms 62, there can be any number in varying embodiments.

Secondary attachment mechanism 64 is shown as a T-slot interface where component 60 has a T-slot fastener 68 that may be slid into T-slot socket 66. T-slot fastener 68 includes a stem and a head. T-slot socket 66 is integrated into the rotary member 13 in this embodiment. In an alternative embodiment, socket 66 may be attached to rotary member 13. T-slot fastener 68 is integrated into component 60 in this embodiment. In an alternative embodiment, fastener 68 may be attached to component 60. Secondary attachment mechanism 64 is a safety device in one embodiment. In normal operation conditions shown in FIG. 3, the secondary attachment mechanism 64 is not engaged and is bearing no component load, or weight. Thus, FIG. 3 shows no part of fastener 68 pressed flush against rotary member 13. Not bearing load during normal operation keeps it as strong as possible and reduces wear. While FIG. 3 shows two secondary attachment mechanisms 64, there can be any number in varying embodiments.

A T-slot interface can be described in one embodiment as a socket having a base defining a recess bordered by a lip, and a fastener having an elongate stem portion and a head slidably insertable into the recess of the socket where it is retained by the lip of the socket.

Figure 4:
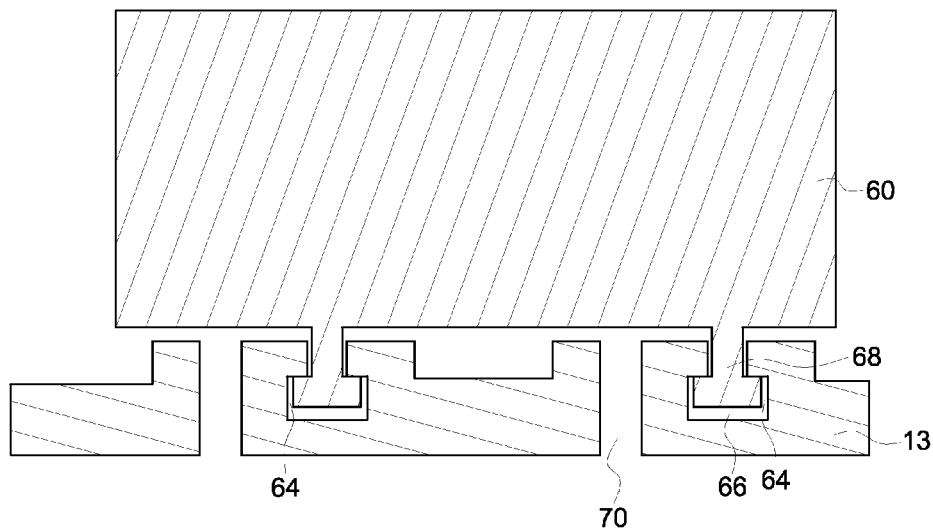
FIG. 4 is a side view of a component attached to a rotary member with a secondary attachment mechanism in accordance with an embodiment.

FIG. 4 shows a system where primary attachment mechanisms are not installed and secondary attachment mechanisms 64 are engaged. Slots 70 in rotary member 13 are empty in this example. This could be in a situation where the primary attachment mechanisms were never put into place, fell out, were not torqued enough for secure fastening, were not the right type of mechanism (wrong length, strength, etc.), are fatigued, are broken, or have had some other issue happen to them. This can be considered a failure condition of a primary attachment mechanism. In this situation the secondary attachment mechanism 64 takes the load. This is shown by the head of fastener 68 being flush against the top part socket 66 during rotation as the force pulls component 60 away from rotary member 13. Thus, the secondary attachment mechanisms 64 protect component 60 from being ejected radially or otherwise from the rotary member 13. There also could be a situation where secondary attachment mechanism only takes part of the load, such as when only some of the primary attachment mechanisms are engaged or the primary attachment mechanisms used are weak for some reason.

According to one embodiment, the gaps within the secondary attachment mechanism's T-slot interface allow for audible noise to be made when the secondary attachment mechanism 64 is engaged. This can alert a nearby human operator to notice that the gantry 12 is running in safety, or failsafe, mode and not in normal mode so the operator can attend to the safety issue. The system can be arranged so that the audible noises are only during gantry 12 spin-up and spin-down or all the time during operation. According to an alternative embodiment, the gaps are such that no audible noise can be heard.

The automatic engaging of the secondary attachment mechanism 64 is a failsafe. This can be desirable since a field engineer may not activate the failsafe if it is manual. A manual installed failsafe is subject to incorrect installation itself. According to some embodiments, the system can automatically engage and requires no manual intervention to activate the failsafe protection. Once the component 60 is in place, it will not be thrown from the rotating structure even without any primary attachment mechanisms 62 installed.

Figure 5:
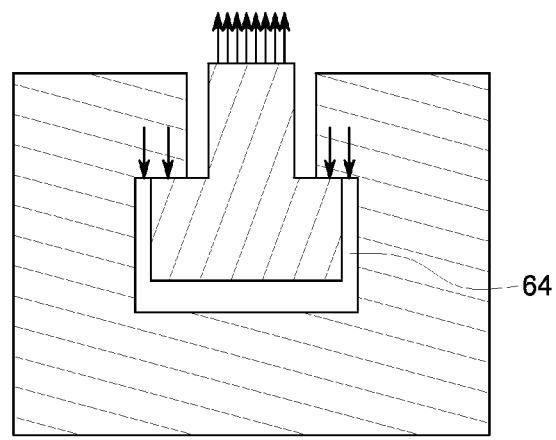
FIG. 5 is a side view of an engaged secondary attachment mechanism in accordance with an embodiment.

FIG. 5 shows an engaged secondary attachment mechanism 64. The design of the secondary attachment mechanism 64 results in substantially even force distribution since load is being carried by both sides of the T-shape according to one embodiment. This increases strength and reliability for the secondary attachment mechanism.

Figure 6:
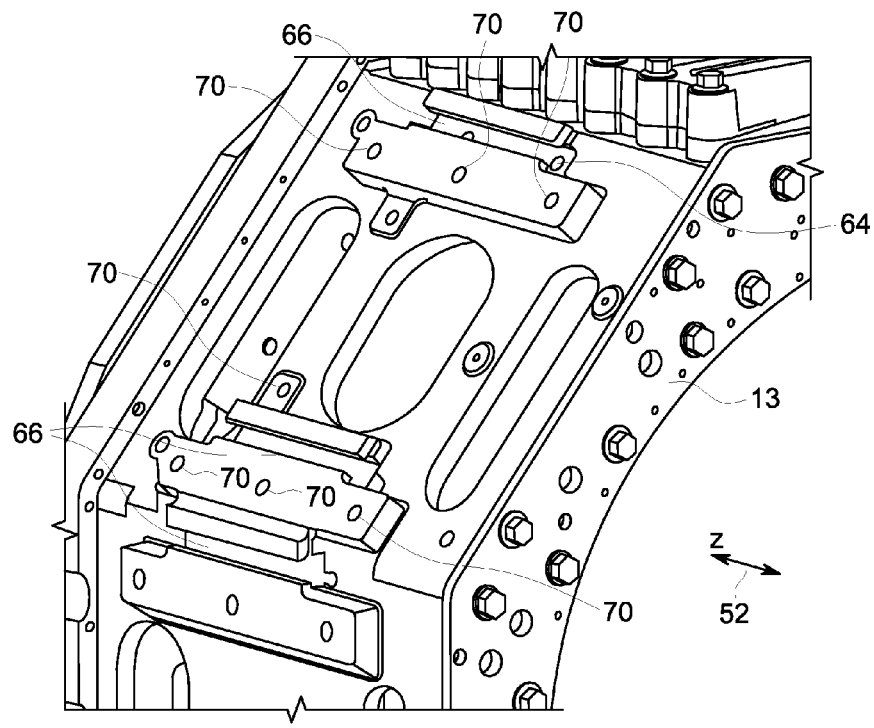
FIG. 6 is an angled view of a rotary member with a t-slot socket in accordance with an embodiment.

FIG. 6 shows an angular view of rotary member 13 that includes one part of the secondary attachment mechanism 64, the t-slot socket 66. A component 60 is first slid in the Z-direction 52 into the rotary member 13. Then primary attachment mechanisms can be installed through slots 70. The slot 70 arrangement shown in FIG. 6 is exemplary. There can be one or more slots 70 and set in various arrangements in rotary member 13.

Figure 7:
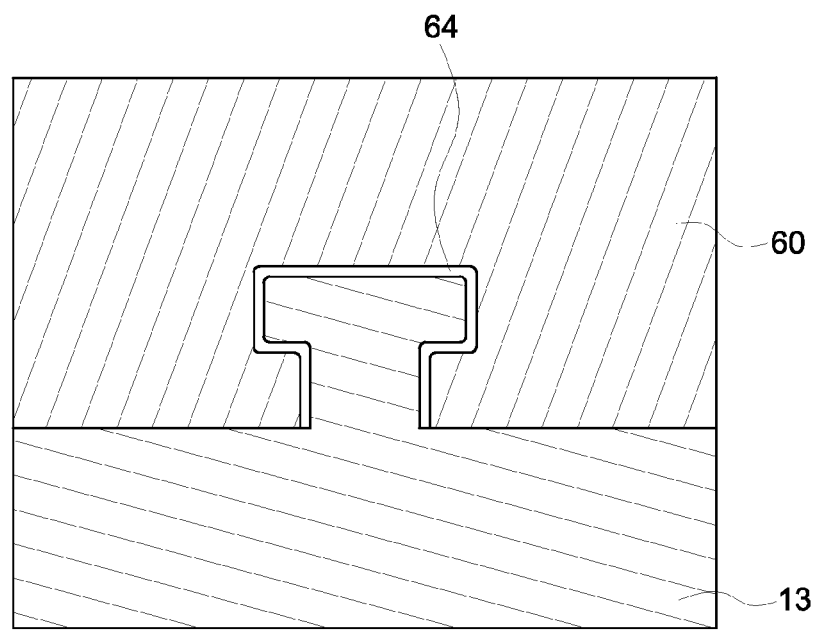
FIG. 7 is a side view of a component attached to a rotary member in accordance with an embodiment.

FIG. 7 shows a view of secondary attachment mechanism 64 in an alternative embodiment. The T-slot fastener is integrated, or attached to, the rotary member 13. The T-slot socket is integrated, or attached to, component 60.

Figure 8:
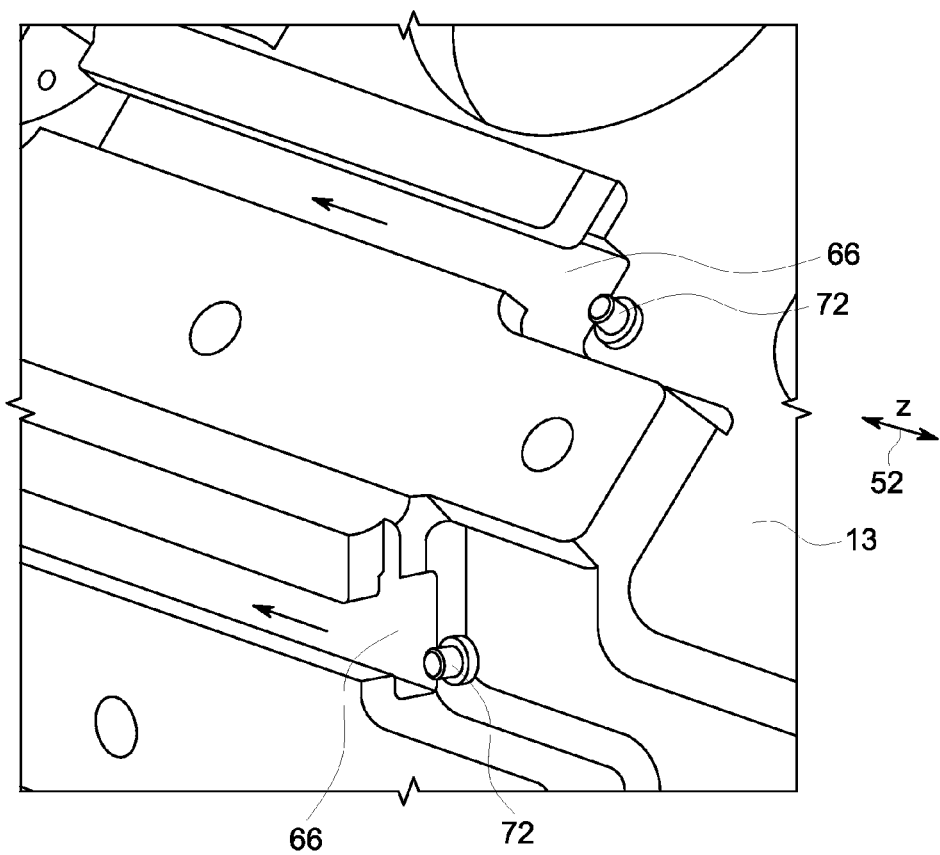
FIG. 8 is an angled view of a rotary member with a t-slot socket and a latch in accordance with an embodiment.
Figure 9:
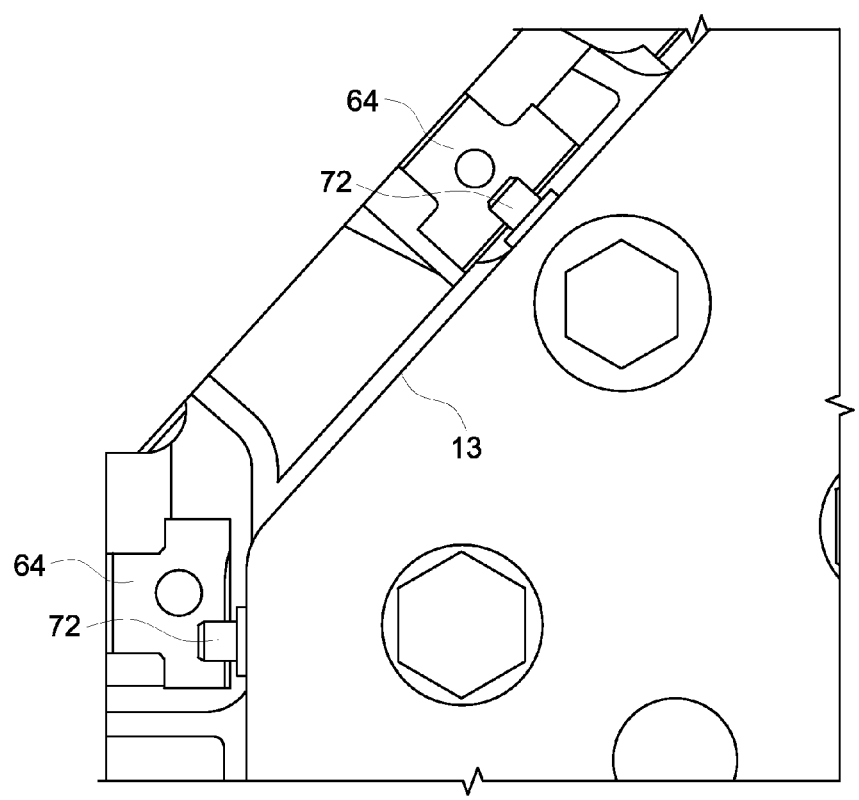
FIG. 9 is a side view of a rotary member with a t-slot socket and a latch in accordance with an embodiment.

FIGS. 8 and 9 show views of rotary member 13 that includes latch 72. Latch 72 depresses as a component slides across it and into socket 66. FIG. 8 shows an angled view. FIG. 9 shows a front view. A component with t-slot fastener could slide into rotary member 13 in the direction of the arrow shown in the sockets 66 in FIG. 8. After the component has fully slid into socket 66, the latch rises to secure the component fastener into place in the axial or Z-direction 52. Thus, the latch retains the component in the rotary member 13 t-slot socket 66 in the axial or Z-direction 52. The latch can also be referred to a Z-capture device, spring pin, or other names common to the art. It is a spring pin with a spring mechanism in one example embodiment.

In the design of one embodiment, latch 72 is automatically engaged. It can be disengaged by manual user input or insertion of a component into the gantry's rotary member 13. Latch 72 cannot be left in a disengaged condition in this embodiment. When a user input to the latch is removed or the component is fully inserted, the latch automatically returns to its engaged state. Latch 72 is further held in place when rotational forces push outward in the radial direction.

Figure 10:
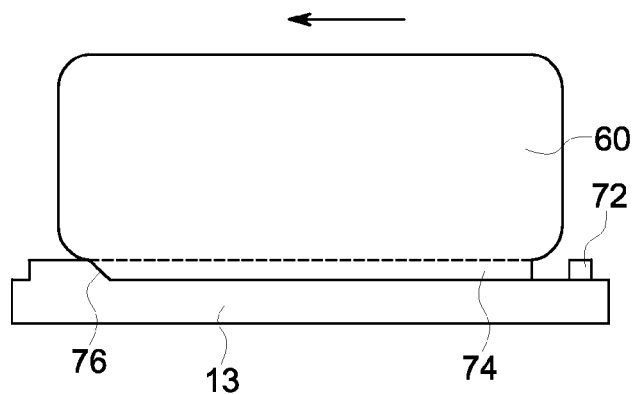
FIG. 10 is a side view of a component inserted into a rotary member in accordance with an embodiment.

FIG. 10 shows a side view of a component 60 inserted into rotary member 13 using the secondary attachment mechanism according to one embodiment. The t-slot fastener head 74 has an angled edge 76 that depresses latch 72 as component 60 is slid into the secondary attachment mechanism of rotary member 13 along the Z-direction of the arrow in FIG. 10. After component 60 is fully inserted, latch 72 automatically rises to block the removal of component 60 without manual input. Angled edge 76 can also be known as a chamfer or ramp.

Figure 11:
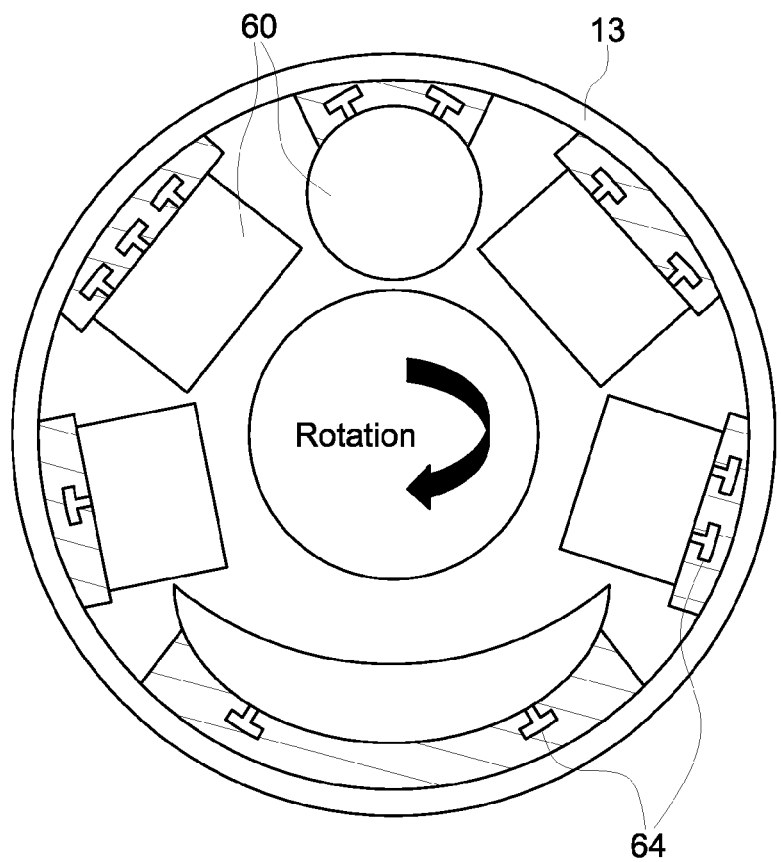
FIG. 11 is a view of components attached to a rotary member in accordance with an embodiment.

FIG. 11 shows additional embodiments of the system. Rotary member 13 has thus far been shown with components 60 on the outside of the rotary member 13. FIG. 11 shows components 60, of various shapes and sizes, attached or mounted to the inside of rotary member 13. Primary attachment mechanisms are still part of the system, but are not shown in the drawing. Secondary attachment mechanisms 64 are shown, sometimes with one, two, or three per component 60 to show the flexibility of the system. In an alternative embodiment, components can be placed on both the inside and outside of rotary member 13.

Figure 12:
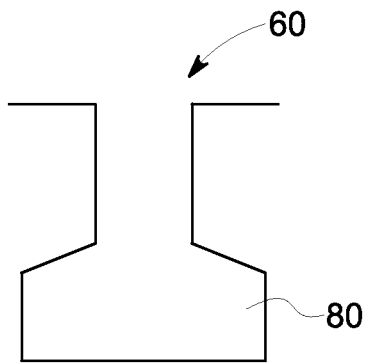
FIG. 12 is a side view of a dove-tail shaped t-slot fastener head in accordance with an embodiment.

FIG. 12 shows a side view of component 60 where the t-slot fastener head 80 is dove-tail shaped, according to one embodiment. This is an example of another t-slot fastener and socket design that could be used.

Figure 13:
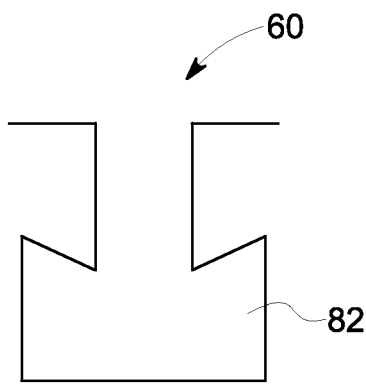
FIG. 13 is a side view of a hook shaped t-slot fastener head in accordance with an embodiment.

FIG. 13 shows a side view of component 60 where the t-slot fastener head 82 is hook shaped, according to one embodiment. This is an example of another t-slot fastener and socket design that could be used. Other t-slot fastener and socket designs can be used as are common to the art. The receiving sockets can also be fashioned to best accept the specific fastener design.

The system disclosed provides useful safety mechanisms for gantries. It provides a secondary attachment mechanism that is not under load during normal operation. When a secondary attachment mechanism is engaged for safety reasons due to an issue with primary attachment mechanism, the system can generate an audible noise for an operator to hear and address the issue. The system also provides additional safety capability by providing an automatic latch to prevent any sliding of the secondary attachment mechanism in the Z-direction.

It should be noted that the secondary attachment mechanism is a backup safety mechanism in some embodiments, but can also be simply a second attachment mechanism that also carries simultaneous load in other embodiments.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A gantry for a tomography system, comprising:
   a stationary support structure;
   a rotary member with an opening for insertion of a subject, wherein the rotary member is attached to the support structure;
   a component;
   wherein the component can be attached to the rotary member by a primary attachment mechanism;
   wherein the component can be attached to the rotary member by a secondary attachment mechanism, the secondary attachment mechanism being a T-slot interface; and
   wherein during rotation of the rotary member, the secondary attachment mechanism does not support the weight of the component if the primary attachment mechanism is engaged.

2. The gantry of claim 1, wherein:
   the primary attachment mechanism is one or more bolts.

3. The gantry of claim 1, the T-slot interface further comprising:
   a socket securable to a first member and having a base defining a recess bordered by a lip;
   a fastener having an elongate stem portion securable to a second member and a head slidably insertable into the recess of the socket where it is retained by the lip of the socket; and
   wherein the first member is the rotary member and the second member is the component, or the first member is the component and the second member is the rotary member.

4. The gantry of claim 3, wherein:
   the fastener head is shaped in a T-shape.

5. The gantry of claim 3, wherein:
   the fastener head is shaped in a dove-tail shape.

6. The gantry of claim 3, wherein:
   the fastener head is shaped in a hook shape.

7. The gantry of claim 1, the T-slot interface further comprising:
   a t-slot socket integrated into the rotary member; and
   a t-slot fastener integrated into the component.

8. The gantry of claim 1, the T-slot interface further comprising:
   a latch for securing a t-slot fastener in place to prevent axial movement of the fastener from a t-slot socket.

9. The gantry of claim 8, wherein:
   the t-slot fastener includes an angled edge on an insertion side; and
   the angled edge depresses the latch as the t-slot fastener is slid into the t-slot socket.

10. The gantry of claim 8, wherein the latch comprises a spring pin.

11. The gantry of claim 1, wherein:
    during rotation of the rotary member, if the primary attachment mechanism is not engaged, the secondary attachment mechanism supports the weight of the component.

12. The gantry of claim 1, wherein:
    during rotation of the rotary member, if the primary attachment mechanism is partially engaged, the secondary attachment mechanism supports the remaining weight of the component.

13. The gantry of claim 1, wherein:
    the component is an x-ray tube, high voltage generator, heat exchanger, collimator, image detector, circuit board chassis, balance weight, or power supply.

14. The gantry of claim 1, wherein:
    the component is attached to the rotary member on the outside of the rotary member.

15. The gantry of claim 1, wherein:
    the component is attached to the rotary member on the inside of the rotary member.

16. A gantry, comprising:
    a stationary support structure;
    a rotary member with an opening for insertion of a subject, wherein the rotary member is attached to the support structure;
    a component;
    wherein the component can be attached to the rotary member by a primary attachment mechanism; and
    wherein the component can be attached to the rotary member by a secondary attachment mechanism, the secondary attachment mechanism being a T-slot interface; and
    wherein during rotation of the rotary member, if the primary attachment mechanism is not engaged, the secondary attachment mechanism supports the weight of the component and the t-slot interface generates a human-audible noise.

17. The gantry of claim 16, wherein:
    the component is attached to the rotary member on the outside of the rotary member.

18. The gantry of claim 16, the T-slot interface further comprising:
    a latch for securing a t-slot fastener in place to prevent axial movement of the fastener from a t-slot socket.

19. The gantry of claim 18, wherein:
    the t-slot fastener includes an angled edge on an insertion side; and
    the angled edge depresses the latch as the t-slot fastener is slid into the t-slot socket.

20. The gantry of claim 18, wherein the latch comprises a spring pin.

21. The gantry of claim 16, wherein:
    the component is an x-ray tube, high voltage generator, heat exchanger, collimator, image detector, circuit board chassis, balance weight, or power supply.

22. A rotary member, comprising:
    at least one slot to accept a primary attachment mechanism;
    at least one socket as part of a secondary attachment mechanism, the socket having a base defining a recess bordered by a lip; and
    wherein the primary and secondary attachment mechanisms can be used to attach a component to the rotary member, and the secondary attachment mechanism does not support the weight of the component if the primary attachment mechanism is engaged.

23. The rotary member of claim 22, wherein:
    the rotary member is annular.

24. The rotary member of claim 22, wherein:
    the component is attached to the rotary member on the outside of the rotary member.

25. The rotary member of claim 22, wherein:
    the component is an x-ray tube, high voltage generator, heat exchanger, collimator, image detector, circuit board chassis, balance weight, or power supply.

26. The rotary member of claim 22, wherein:
    the component is attached to the rotary member on the inside of the rotary member.

* * * * *